United States Patent

Ritter

Patent Number: 6,059,728
Date of Patent: May 9, 2000

[54] THREE-DIMENSIONAL ULTRASOUND IMAGING SYSTEM AND PROBE

[75] Inventor: John Alan Ritter, Des Peres, Mo.

[73] Assignee: Storz Instrument Co., St. Louis, Mo.

[21] Appl. No.: 08/987,721

[22] Filed: Dec. 9, 1997

Related U.S. Application Data

[60] Provisional application No. 60/035,346, Jan. 2, 1997.

[51] Int. Cl.$^7$ .................................................. A61B 8/00
[52] U.S. Cl. ........................................ 600/443; 600/459
[58] Field of Search ................................ 600/441, 443, 600/439, 446, 459, 447, 409; 128/916

[56] References Cited

U.S. PATENT DOCUMENTS

| | | | |
|---|---|---|---|
| 3,090,771 | 5/1963 | Pickering et al. | 340/1 |
| 4,381,787 | 5/1983 | Hottinger | 128/660 |
| 4,407,293 | 10/1983 | Suarez et al. | 128/660 |
| 4,509,525 | 4/1985 | Seo | 128/663 |
| 4,566,459 | 1/1986 | Umemura et al. | 128/660 |
| 4,664,123 | 5/1987 | Iinuma | 128/660 |
| 4,866,614 | 9/1989 | Tam | 364/413.25 |
| 4,972,838 | 11/1990 | Yamazaki | 128/661.09 |
| 5,027,820 | 7/1991 | Pesque | 128/660.07 |
| 5,060,651 | 10/1991 | Kondo et al. | 128/660.07 |
| 5,078,145 | 1/1992 | Furuhata | 128/660.07 |
| 5,159,931 | 11/1992 | Pini | 128/660.07 |
| 5,282,471 | 2/1994 | Sato | 128/916 |
| 5,322,067 | 6/1994 | Prater et al. | 128/916 |
| 5,379,769 | 1/1995 | Ito et al. | 128/916 |
| 5,441,052 | 8/1995 | Miyajima | 600/455 |
| 5,474,073 | 12/1995 | Schwartz et al. | 128/916 |
| 5,503,152 | 4/1996 | Oakley et al. | 600/447 |

*Primary Examiner*—Marvin M. Lateef
*Assistant Examiner*—Maulin Patel
*Attorney, Agent, or Firm*—Grant D. Kang

[57] ABSTRACT

The invention is a linear transducer array having an axis of rotation parallel to the long axis of the array. Accordingly, each transducer element is analogous to the single transducer of the traditional B-scan. All the elements are pulsed in rapid sequence as the entire array is swept mechanically, and a series of B-scan planes, displaced from each other by the transducer element spacing, are created. Display control electronics interpret the multiple planes with the resultant solid volume represented in isometric or perspective views on a CRT. Ultrasonic transducer arrays of 16 or more elements can be fabricated which would cover the entire volume of the eye in a single angular sweep.

4 Claims, 5 Drawing Sheets

THREE-DIMENSIONAL ULTRASOUND IMAGING SYSTEM AND PROBE

This application claims benefit of provisional application 60/035,346 filed Jan. 2, 1997.

BACKGROUND OF THE INVENTION

1. Field of the Invention

This invention relates to ultrasound imaging and, in particular to a system including an ultrasonic probe for generating three-dimensional real images of relatively modest volumes in a body such as the eye, testes, breast, carotid artery, tumors, kidney, liver, etc. within 5 cm of the surface.

2. Related Art

Current ultrasound systems acquire a single two-dimensional image in real-time or near-real time using an ultrasonic probe. The ultrasonic probe uses a single circularly-symmetric transducer crystal which is iterated through multiple transmit and receive cycles. Each cycle acquires a "ray" of information. When the transducer is physically moved through an arc, multiple rays are acquired at different angular positions of the transducer. The intensity of the returning echos is represented by the brightness of the corresponding pixels on a CRT screen, giving rise to the name "b-scan", or "brightness scan" for such devices. Alternatively, three-dimensional images are acquired by first taking a two-dimensional image, physically moving the entire probe, taking a second and subsequent two-dimensional image in a different plane, and merging (i.e. integrating) the multiple images together to form a three-dimensional, non-real time image. This three-dimensional image may take up to six minutes to scan and create.

Two-dimensional images are generated by a transducer, with information regarding the third dimension acquired by physical movement of the transducer. Thus, a set of static images is integrated to produce a three-dimensional image. The physical movements may take a variety of forms.

The physical movement may be linear, with a transducer mounted on a lead screw driven by a motor. Rotating the lead screw moves the transducer in a linear fashion, parallel to the surface scanned. The acquired two-dimensional images are parallel to each other, and separated by pre-defined spatial intervals.

The physical movement may also be a pivoting movement, also know as fan scanning. The transducer/imaging plane is rotated about an axis at the transducer face and produces an angular sweep with a fan of planes each with a predefined angular separation. The angular step between acquired planes is fixed. Accordingly, the distances between sampled regions depend on depth. The sampling distances are small near the transducer where the elevational resolution is fine. But the sampling distances are large further away from the transducer where the elevational resolution is poor.

Both the linear scanning and the fan scanning approaches are described in greater detail in the November/December 1996 issue of IEEE Engineering In Medicine and Biology Magazine, Volume 15, Number 6.

Regardless of the physical movement employed, data acquisition is limited primarily by the speed with which the transducer can be swept through its arc, and generally provides from 15 to 30 frames per second. High frame rates are desirable for visualization of dynamic processes, which includes visualization of vascular motion during tumor diagnosis, monitoring of the motion of retinal detachments and vitreous hemorrhages, and detection of foreign bodies within the vitreous. Modern B-scans provide digital storage for the display data, allowing a particular frame to be retained, or "frozen", for closer examination.

A two-dimensional image does not eliminate risk of misdiagnosis due to a lack of complete information. Similarly, a three-dimensional image which is not real time, or near real time, carries the same risk because the three-dimensional integrated image requires that the position and orientation of the two-dimensional scan plane be known for each separate image, and that the eye or other object of interest remain still for the duration of the examination. However, during ophthalmic B-scan exams, it is frequently critical that the patient move his or her eye in order for the operator to visualize the motion of the vitreous and any membranes, such as from retinal detachments, which may be present. Any such motion clearly renders static data acquisition impossible, since the position of the eye from scan to scan is then unknown.

Generally, two-dimensional B-scan data is acquired by digitizing the video output from an existing B-scan. The digitizing step necessarily requires some loss of resolution or image quality.

Alternatively, information regarding the third dimension may be acquired by replacing physical movement of the transducer by electronic scanning. Specifically, a two-dimensional array of transducers generates a pulse of ultrasound which diverges away from the array in a pyramidal shape. The echos are processed to generate three-dimensional information in real time. However, two-dimensional arrays are not yet practical because of low yields resulting from the manufacture of a large number of small elements, along with the connecting and bundling of large numbers of leads.

Accordingly, there is a need in the art to provide a near real time, or real time three-dimensional imaging system and probe capable of transmitting and receiving acoustic signals for such a system. Such a system would improve visualization of modest volumes such as posterior ocular structures and thus improve diagnosis of tumors, retinal detachments, foreign bodies, etc. In addition, since such a system would acquire volumetric images in real time or near real time, several images may be acquired in sequence to allow three-dimensional visualization of motion by stepping sequentially through the different three-dimensional images, providing even better visualization of motion of the intraocular contents.

There is a further need in the art to provide an imaging system which does not require digitizing video output. Instead, there is a need to acquired volumetric images in real-time in sequence, and store the images for processing in a three-dimensional display format which would allow three-dimensional visualization of motion by stepping sequentially through the different three-dimensional images, to provide better visualization of motion of intraocular contents.

SUMMARY OF THE INVENTION

It is in the view of the above problems that the present invention was developed. The invention is a linear transducer array having an axis of rotation parallel to the long axis of the array. Accordingly, each transducer element is analogous to the single transducer of the traditional B-scan. All the elements are pulsed in rapid sequence as the entire array is swept mechanically, and a series of B-scan planes, displaced from each other by the transducer element spacing, are created. Display control electronics interpret the multiple planes with the resultant solid volume represented in isometric or perspective views on a CRT. Ultrasonic transducer arrays of 16 or more elements can be fabricated which would cover the entire volume of the eye in a single angular sweep.

Further features and advantages of the present invention, as well as the structure and operation of various embodiments of the present invention, are described below in detail with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Referring to the accompanying drawings in which like reference numbers indicate like elements, FIGS. 1a–1d show an ultrasonic probe of the present invention shown generally at 10. Ultrasonic probe comprises housing 12 and a transducer assembly 14 as discussed in greater detail below in connection with the discussion of FIGS. 4 and 5.

Figure 1D:
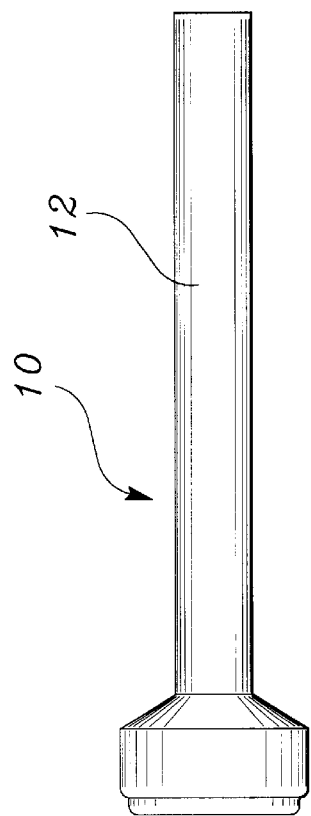
FIG. 1d illustrates a plan side view of the ultrasonic probe of the present invention.
Figure 1A:
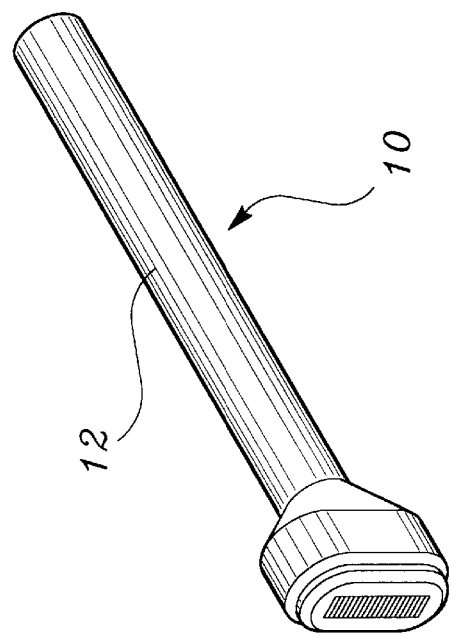
FIG. 1a illustrates a perspective view of an ultrasonic probe of the present ultrasound imaging system of the invention.
Figure 1C:
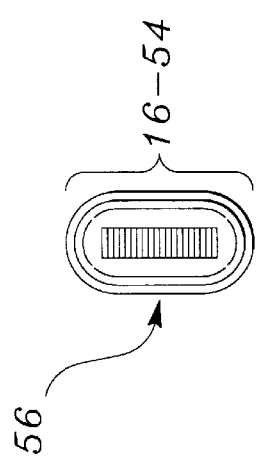
FIG. 1c illustrates a front plan view of the ultrasonic probe and a linear transducer array of the present invention.

Transducer assembly 14 comprises a plurality of single crystal transducers, here twenty, 16–54, respectively disposed in a linear array as shown in FIG. 1c. One of the advantages of a single-crystal transducer is that it may be ground to produce a focused beam of ultrasound. This improves resolution within the eye to less than 1 millimeter. By contrast, a non-focused single-crystal transducer, and, by extension, a flat-faced linear array will have a basic resolution transverse to the beam no better than its element size. Focusing in the plane perpendicular to the array's long dimension may be effected by producing a cylindrically-symmetric array. It is also possible to electronically focus a beam of sound by properly phasing the transmit trigger and receive signals from groups of adjacent transducer elements. This forms the foundation for the present invention.

Figure 1B:
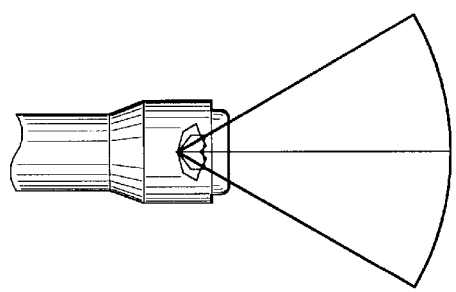
FIG. 1b illustrates a 60 degree angular sweep by the transducer array of the present invention.
Figure 2:
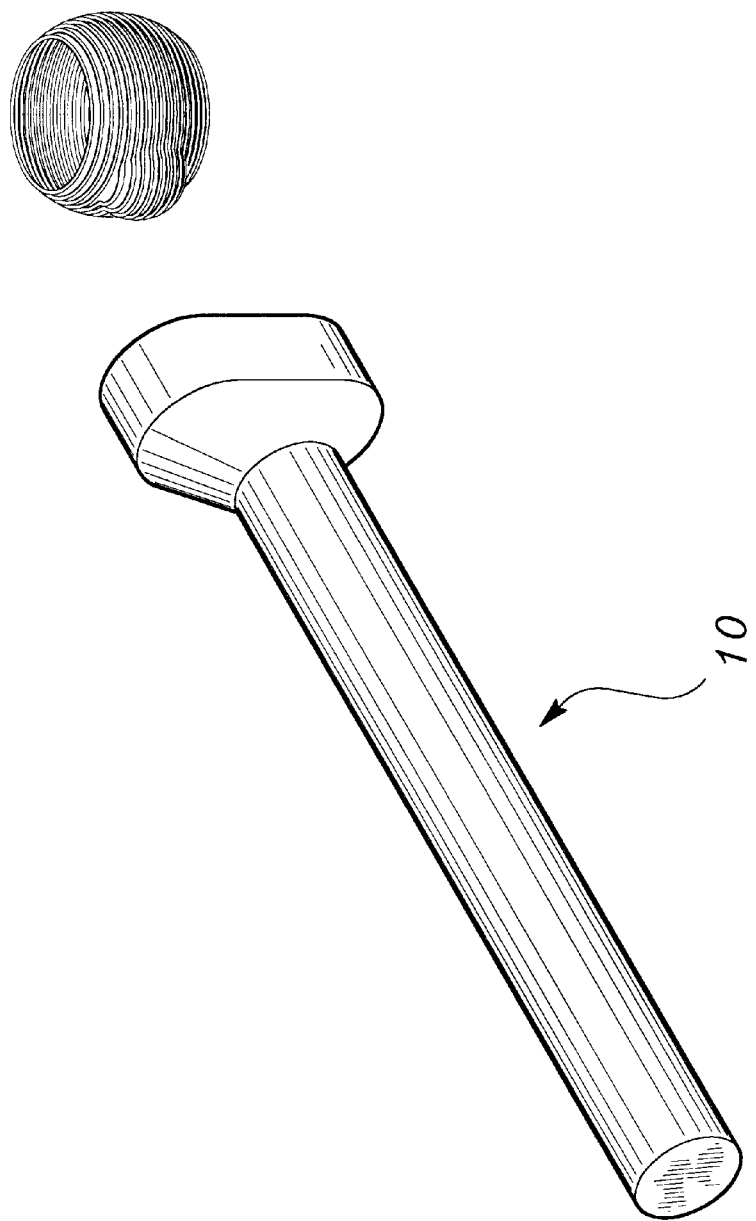
FIG. 2 illustrates a perspective view of the ultrasonic probe of the present invention as used on an eye-volume.

The transducer array shown generally at 56 may be rotated to sweep a 60 degree arc as shown in FIG. 1b. Thus as shown in FIG. 2, as ultrasonic probe 10 is presented to an eye, the transducer array 56 may sweep a 60 degree arc across a small volume such as the eye. As transducer array 56 sweeps an arc, the array emits a series of pulses, with each pulse acquiring a slice of information. Accordingly, in FIG. 3, four separate slices are shown in a side plan view of probe 10.

Figure 3:
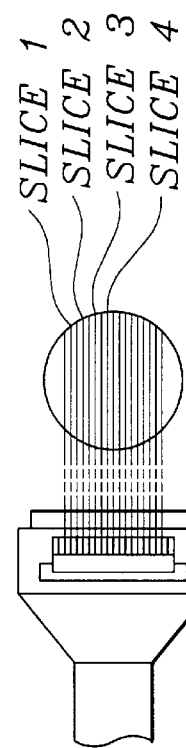
FIG. 3 illustrates various image slices using the ultrasonic probe of the present invention.
Figure 3:
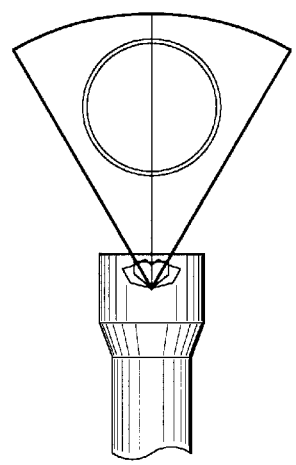
Figure 3:
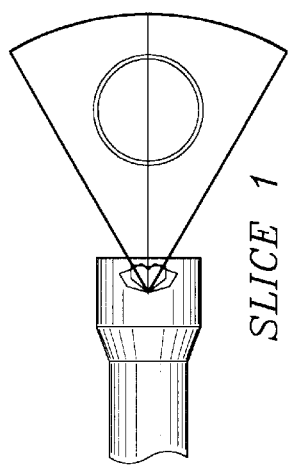
Figure 3:
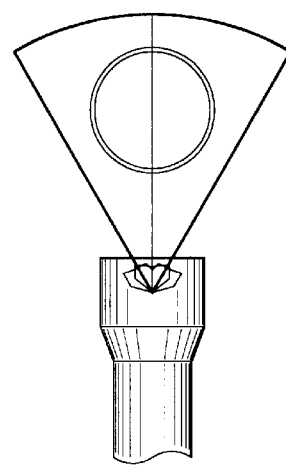
Figure 3:
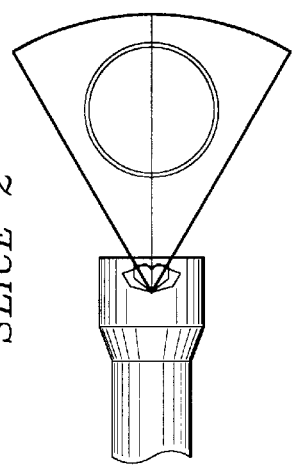

FIG. 3 illustrates schematically how the relationship between slices which make up an image. In this example, the probe is positioned near an "eyeball" which is modeled as a hollow sphere. Four representative slices are shown, from the top element, two intermediate elements, and the element corresponding to the equatorial plane of the scanned sphere. The top plan view of probe 10 in FIG. 3 illustrates a series of pulses emitted from transducer array 56 in further shows that the individual pulses from each transducer, 16–54, have a phased transmit. If all 16 slices are combined in an isometric view, the resultant three-dimensional representation of the eyeball may be obtained.

Figure 4:
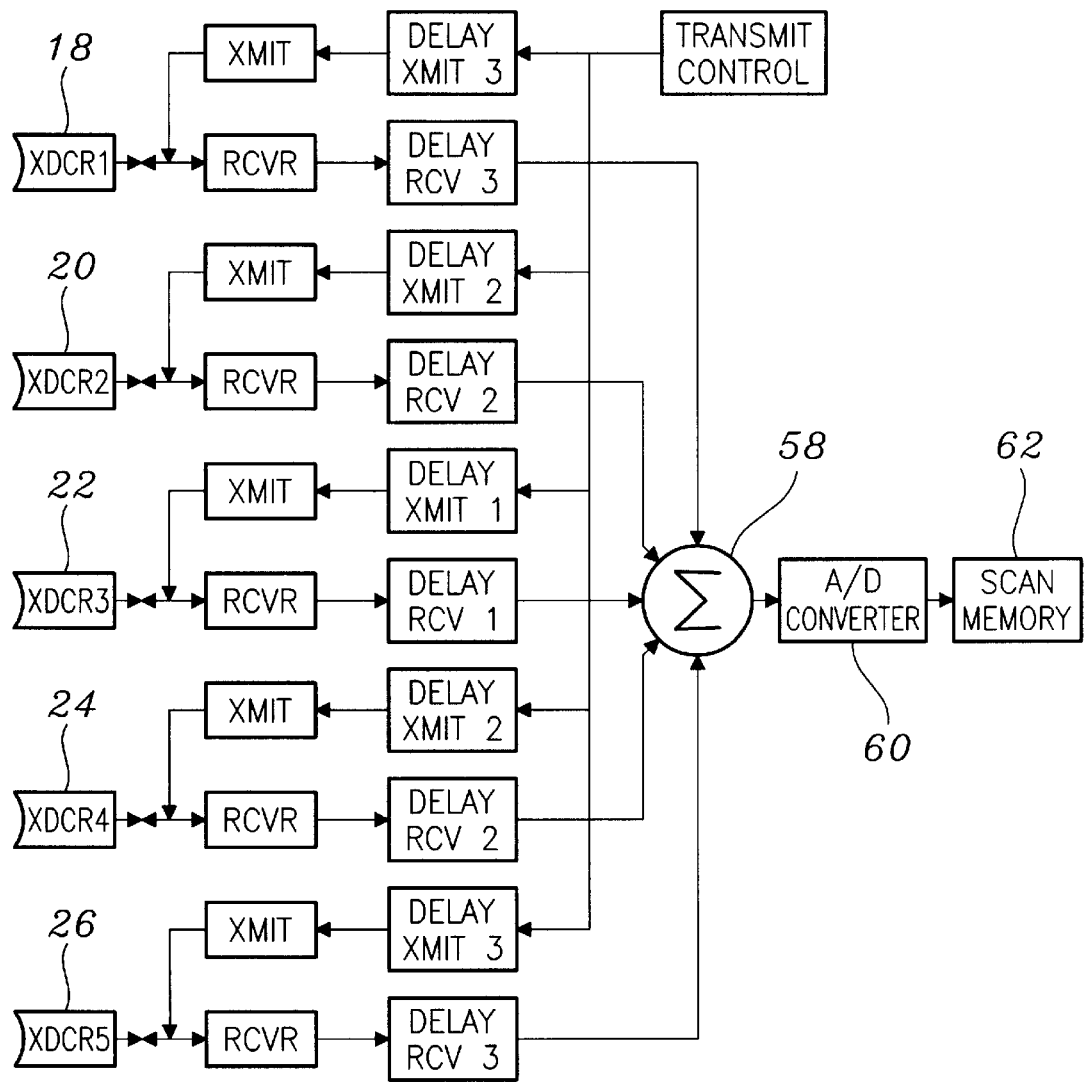
FIG. 4 illustrates a five transducer array as a basic unit of the present invention.

Turning to FIG. 4, if it is desired to acquire information on 16 planes of 1 millimeter thickness, an electronic system which phases groups of five transducer elements, 18–26, respectively, and allows theoretical lateral resolution on the order of 0.5 to 0.75 millimeters, a focal point at 20 millimeters from the transducer array, and a 6 dB focal zone extending from about 13 to 40 millimeters, is preferred. At the far 6 dB point, the beam has expanded to approximately 1.5 millimeters in diameter. By producing a linear array 5 millimeters in width with a cylindrical radius of 20 millimeters, the resolution in the transverse plane can be achieved. The system resolution axial to the beam will be determined primarily by the excitation waveform, transducer ringdown, and receiver filtering characteristics. Typically, the axial resolution is at least as good as the transverse resolution, but must be optimized versus sensitivity and signal-to noise of the acquired image.

Using five transducers simultaneously, and acquiring 16 planes, requires a total of 20 transducer elements in the array: the sixteen elements corresponding to the center elements of the 16 planes, plus two elements to either side of the outermost plane-center elements. Since the phasing on the end element of two adjacent groups of five would clearly be the same, the groups may overlap by one element, with the signal from the shared element electronically duplicated for combination into the two planes' individual signals. FIGS. 1a–1d illustrate one possible configuration for such a probe in front, side, top, and isometric view (upper left corner) and representative angular position of the array are shown in the top view, with an indication of the arc covered as the array is swept through 60 degrees.

Thus, looking at the action of a single five-transducer-element group as in FIG. 4, outer transducer elements 18 and 26 are provided with the same transmit time, transducer elements 20 and 24 have the same transmit time which time is different from the transmit time of the outer transducer elements 18 and 26, and the center transducer has a transmit time different from the previous two transducer times. Accordingly, the transmissions from the five transducers 18–26 are phased into three separate transmit times. In practice, the outer transducers 18–26 transmit first followed by the inside transducers 20 and 24, and finally followed by the center transducer 22. The reflected signal from the body volume (eye) is similarly received by each of the transducers 18–26. As seen in FIG. 4, the transducers have phased reception of the reflected signals. These signals are accumulated at 58 and later converted by A/D converter 60, and ultimately stored into memory 62.

Figure 5:
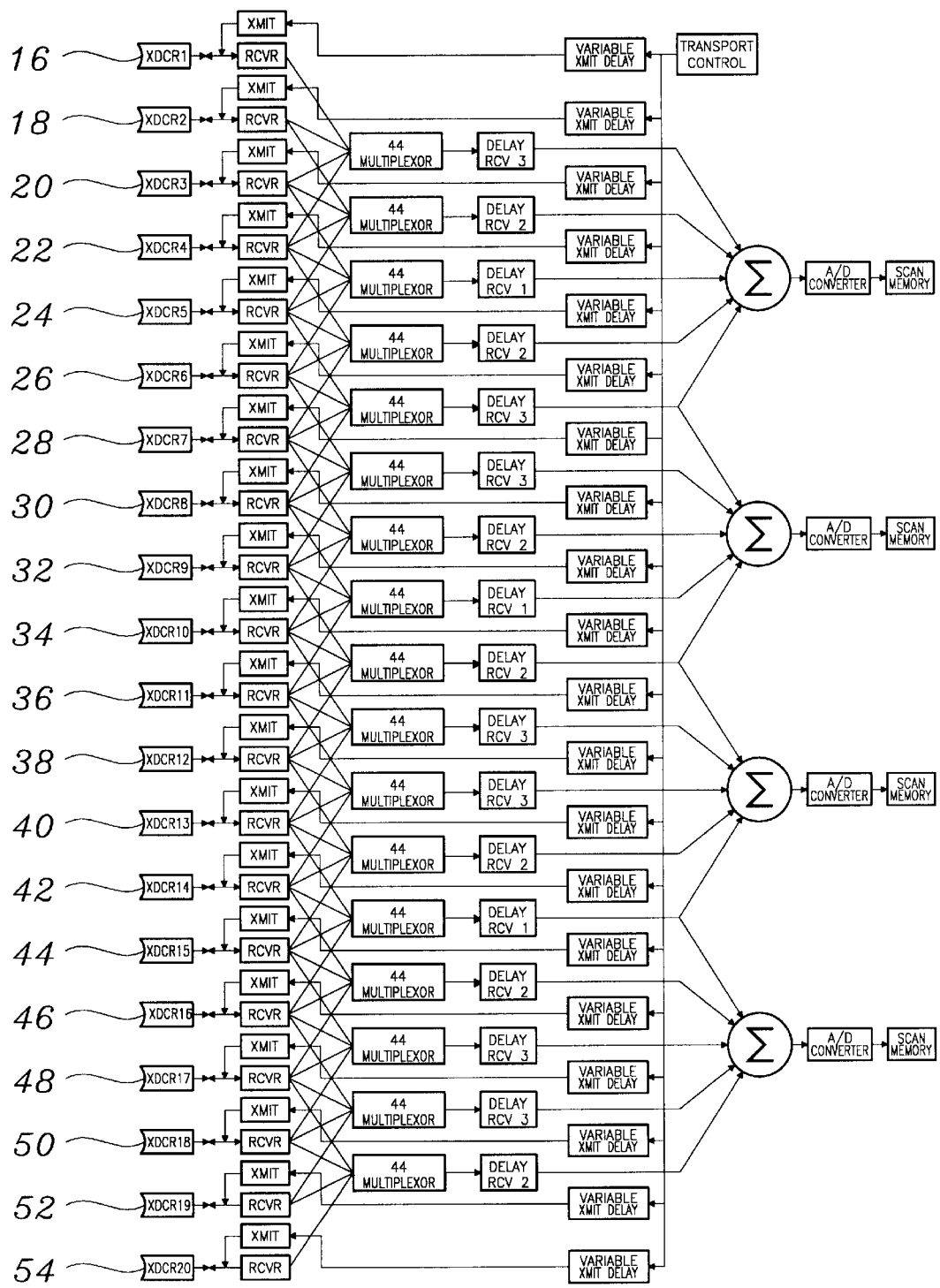
FIG. 5 illustrates a 20 transducer array forming a complete unit of the present invention.

In order to speed up the data acquisition, four groups of five elements may be pulsed simultaneously. Thus, FIG. 5 shows 20 transducer elements, 18–54, respectively in a linear transducer array 56. A slight modification of the arrangement in FIG. 4 for efficiency has been introduced by use of an intermediate multiplexor. To make this arrangement possible, a critical feature of the invention is that a rod is commonly disposed through all the transducers such that the longitudinal axis of the rod is parallel to the longitudinal axis of the array. It is noted that the linear array of transducers 56 is preferably longitudinally concave for improved performance.

Introduction of multiple five-transducer groups in FIG. 5 permits an additional phasing opportunity in the form of group indexing. The first group of five transducers, 16–24, takes the first slice of information with the transducer transmissions phased as discussed in FIG. 4. The second group of five transducers, 24–32, takes the second slice of information with the transducer transmissions phased. The third group of five transducers, 32–40, takes the third slice of information. The fourth group of transducers, 40–48, takes the fourth slice of information. All four slices are taken simultaneously. As stated earlier, the groups may overlap by one element, with the signal from the shared element electronically duplicated for combination into the two planes' individual signals. Next, the groups themselves are "phased" by indexing the group itself. Specifically, after taking the first four slices of information simultaneously, the first group of transducers electronically "indexes" by one transducer such that it now consists of transducers 18–26, the second group consists of transducers 26–34, the third group consists of transducers 34–42, and the fourth of transducers 42–50. Thus, with the first group, transducers 18 and 26 transmit simultaneously, and transducers 20 and 24 transmit simultaneously and after transducers 18 and 26, in a manner as described in conjunction with FIG. 4. With these new groups, four more slices of information are obtained simultaneously.

Then, the groups electronically index again such that first group of transducers consist of transducers 20–28, the second group consists of transducers 28–36, the third group consists of transducers 36–44, and the fourth consists of transducers 44–52. Thus, with the first group, transducers 20 and 28 transmit simultaneously, and transducers 22 and 30 transmit both simultaneously and after transducers 20 and 28, in a manner as described in conjunction with FIG. 4. As a result, four more slices of information are obtained simultaneously, one slice from each transducer group.

After a third indexing and taking four more slices, all the transducers will have been utilized and 16 slices of information will have been obtained. When this occurs, the rod on which the linear array 56 is mounted is incrementally rotated by a fixed angle. At this new angle relative to the body volume, the four groups of transducers are again electronically indexed and 16 more slices of information are taken. When the rod has rotated the transducers through a sixty degree arc, the sweep is complete. It is readily appreciated by those with skill in the art that the electronic indexing of the transducer groups for transmit must also apply to the electronic indexing of the transducer groups for receiving.

It is this particular combination of linear array, phasing of transducer transmit and receive signals, and indexing of transducer groups in sequence which makes novel the present invention.

Alternatively, no common transducer element needs to be shared during phasing. Thus, with three transducer groups each having three transducers, an alternate method (not shown) of ultrasonic imaging may comprise the steps of: (a) disposing first, second and third ultrasonic transducers in a linear array on a rod; (b) disposing fourth, fifth, and sixth ultrasonic transducers in said linear array on said rod; (c) disposing seventh, eighth, and ninth ultrasonic transducers in said linear array on said rod; (d) phasing transmit trigger signals from said first, second, third, fourth, fifth, and sixth ultrasonic transducers such that in a transmit trigger instance said first, third, fourth, and sixth ultrasonic transducers are triggered first, and said second and fifth transducers are triggered next; and (d) indexing the phase of the transmit trigger signals from said first, second, third, fourth, fifth, sixth, and seventh ultrasonic transducers such that in the next transmit trigger instance said second, fourth, fifth, and seventh transducers are triggered first, and said third and sixth transducers are triggered next; (e) indexing the phase of the transmit trigger signals from said first, second, third, fourth, fifth, sixth, seventh, and eighth ultrasonic transducers such that in the next transmit trigger instance said third, fifth, sixth and eighth transducers are triggered first, and said fourth and seventh transducers are triggered next; (f) indexing the phase of the transmit trigger signals from said first, second, third, fourth, fifth, sixth, seventh, eighth, and ninth ultrasonic transducers such that in the next transmit trigger instance said fourth, sixth, seventh, and ninth transducers are triggered first, and said fifth and eighth transducers are triggered next; (g) rotating said linear array a fixed angular distance; and (h) repeating steps (c), (d), (e), (f), and (g) until said linear array has rotated a fixed angular distance.

In ophthalmic applications, where the deepest penetration desired is on the order of 75 mm at approximately 1500 meters/second, or approximately 100 microseconds round-trip, each group of sixteen rays is acquired in four transmit/receive cycles, or 400 microseconds. When a sixty-degree arc is swept, with 128 rays in each arc, the theoretical maximum solid frame rate is just under 20 frames per second. Some overhead is required to allow recharging of the transmit power supply and processor control of the data acquisition as is well known in the art. A minimum frame rate of 10 frames per second is achievable and that 15 frames per second is possible. Although these frame rates are at the low end of current two-dimensional systems, the ease of simultaneous visualization of a full three-dimensional image outweighs the disadvantages of a somewhat lower frame rate.

The probe itself does not differ conceptually from existing mechanical sector probes. The primary differences are in the shape of the distal end of the probe, which is now oval, rather than circular, and in the size of the drive motor, as more torque would be required to swing the larger linear array and to overcome the flexing force of multiple transducer wires. Current B-scan probes have body diameters on the order of ½ to ¾ inch, with a ⅝ to ⅞ inch circular contact patch. The three-dimensional probe of the present invention uses a ⅝ inch body diameter, with a ⅝ inch by 1⅛ inch oval contact patch.

Ideally, it is desirable to perform the full three-dimensional display transformation in real time. For the data acquisition system described above, there are 16 planes of 128 rays of 512 samples each, or about 1 million samples per image. If a frame rate of 15 frames per second is required, this requires 15 million three-dimensional to two-dimensional conversions per second. This is clearly beyond the capability of an economical software-driven system, and taxes the state of the art in cost-effective coordinate transformation hardware. However, should such a system become economically feasible, the present invention could be used to provide full three-dimensional display transformation in real-time. For the moment, therefore, the real-time display function will be limited to a single user-selected B-scan plane. The three-dimensional conversion may be a secondary process which might take one or several seconds.

In order to visualize the interior surface of retina, user controls over the viewpoint, truncation planes, and strength of echo considered "transparent" would be provided. Thus the image might be rotated, enlarged, and "clipped" to provide the exact view desired.

The display resolution required is not a particular limitation. The 512 samples in each ray dictate roughly the maximum horizontal resolution in the real-time B-scan mode.

Assuming that NTSC compatibility is required so that images may be recorded and played on a conventional videocassette recorder, the maximum vertical resolution is 480 lines, requiring that the extreme corners of the image be clipped if a full-screen B-scan image is desired. In the isometric three-dimensional view, some additional manipulation will be required to fit the full view into the available format.

In the real-time B-scan mode, a single B-scan plane consists of 512×128 pixels, which, at 15 frames per second, results in a required transformation rate of just less than 1 million pixels per second. Thus, the specified 10 to 15 frames per second data acquisition rates are compatible with real-time transformation of a single B-scan image.

The amount of memory required will be dictated primarily by the number of solid images to be stored simultaneously. One megabyte of memory is required per image. One second of real-time acquisition requires 10 to 15 megabytes at the frame rates discussed above. The decision to increase or decrease this capability should be a function versus cost tradeoff.

In view of the foregoing, it will be seen that the several objects of the invention are achieved and other advantages are attained. The embodiments were chosen and described in order to best explain the principles of the invention and its practical application to thereby enable others skilled in the art to best utilize the invention in various embodiments and with various modifications as are suited to the particular use contemplated. As various modifications could be made in the constructions and methods herein described and illustrated without departing from the scope of the invention, it is intended that all matter contained in the foregoing description or shown in the accompanying drawings shall be interpreted as illustrative rather than limiting. For example, different numbers of transducers in each group may be used, or different numbers of transducers overall may be used. In another example, a three-transducer group may be used in lieu of a five-transducer group, with the outer transducers having a common transmit and receive phase. In another example, the some pivoting means other than a rod may be used to rotate the transducer array, e.g. dual pivot bearings, hinges, two aligned rods which are not connected, pins, or any other means for providing for rotation of the array about any axis parallel to its longitudinal axis. Thus, the breadth and scope of the present invention should not be limited by any of the above-described exemplary embodiments, but should be defined only in accordance with the following claims appended hereto and their equivalents.

What is claimed is:

1. A method of ultrasonic imaging comprising the steps of:
    (a) disposing first, second and third ultrasonic transducers in a single linear array on a rod;
    (b) disposing fourth, fifth, and sixth ultrasonic transducers in said linear array on said rod;
    (c) phasing transmit trigger signals from said first, second, third, fourth, and fifth ultrasonic transducers such that in a transmit trigger instance said first, third, and fifth ultrasonic transducers are triggered first, and said second and fourth transducers are triggered next; and
    (d) indexing the phase of the transmit trigger signals from said first, second, third, fourth, and fifth ultrasonic transducers such that in the next transmit trigger instance said second, fourth, and sixth transducers are triggered first, and said third and fifth transducers are triggered next;
    (e) non-manually rotating said linear array a fixed angular distance; and
    (f) repeating steps (c), (d) and (e) until said linear array has rotated a fixed angular distances
    (g) receiving the transmitted signals reflected back towards the transducer array;
    (h) converting the information in the detected reflected signals to distance measurements, positional coordinates, and echo amplitudes: and
    (i) acquiring real-time three-dimensional information from the use of said single linear array.

2. The method of claim 1, wherein said fixed angular distance is approximately 60 degrees.

3. A method of ultrasonic imaging comprising the steps of:
    (a) disposing first, second, third, fourth, and fifth ultrasonic transducers in a single linear array;
    (b) disposing sixth, seventh, eighth, ninth, and tenth ultrasonic transducers in said linear array;
    (c) phasing transmit trigger signals from said first, second, third, fourth, fifth, sixth, seventh, eighth, and ninth ultrasonic transducers such that in a transmit trigger instance said first, fifth, and ninth ultrasonic transducers are triggered first, said second, fourth, sixth, and eighth transducers are triggered next, and said third and seventh transducers are triggered next;
    (d) indexing the phase of the transmit trigger signals from said first, second, third, fourth, fifth, sixth, seventh, eighth, ninth, and tenth ultrasonic transducers such that in the next transmit trigger instance said second, sixth, and tenth transducers are triggered first, said third, fifth, seventh, and ninth transducers are triggered next, and said fourth and eighth transducers are triggered next;
    (e) non-manually rotating said linear array a fixed angular distance; and
    (f) repeating steps (c), (d) and (e) until said linear array has rotated a fixed angular distance;
    (g) receiving the transmitted signals reflected back towards the linear transducer array;
    (h) converting the information in the detected reflected signals to distance measurements, positional coordinates, and echo amplitudes; and
    (i) acquiring real-time three-dimensional information from the use of said single linear array.

4. The method of claim 3, wherein said fixed angular distance is approximately 60 degrees.

* * * * *